(12) United States Patent
Mihovilovic et al.

(10) Patent No.: US 9,475,787 B2
(45) Date of Patent: Oct. 25, 2016

(54) PROCESS FOR THE PRODUCTION OF FURAN DERIVATIVES

(71) Applicant: ANNIKKI GMBH, Graz (AT)

(72) Inventors: Marko Mihovilovic, Perchtoldsdorff (AT); Michael Schön, Vienna (AT); Johanna Hölbling, St. Georgen/Attergau (AT)

(73) Assignee: Annikki GMBH, Graz (AT)

( * ) Notice: Subject to any disclaimer, the term of this patent is extended or adjusted under 35 U.S.C. 154(b) by 0 days.

(21) Appl. No.: 14/424,372

(22) PCT Filed: Sep. 2, 2013

(86) PCT No.: PCT/EP2013/068051
§ 371 (c)(1),
(2) Date: Feb. 26, 2015

(87) PCT Pub. No.: WO2014/033289
PCT Pub. Date: Mar. 6, 2014

(65) Prior Publication Data
US 2015/0218118 A1    Aug. 6, 2015

(30) Foreign Application Priority Data

Sep. 3, 2012 (EP) ................... 12182758

(51) Int. Cl.
*C07D 307/50* (2006.01)
(52) U.S. Cl.
CPC ................. *C07D 307/50* (2013.01)
(58) Field of Classification Search
USPC ........................................ 549/488
IPC ................................... C07D 307/50
See application file for complete search history.

(56) References Cited

FOREIGN PATENT DOCUMENTS

WO    WO 2012015616 A1 *  2/2012  ............. C07C 67/00

OTHER PUBLICATIONS

Aida et al, "Dehydration of d-glucose in high temperature water at pressures up to 80 MPa", The Journal of Supercritical Fluids, Apr. 2007, pp. 381-388, vol. 40, Issue 3.

Amarasekara et al, "Mechanism of the dehydration of d-fructose to 5-hdryoxymethylfurfural in dimethyl sulfoxide at 150° C.: an NMR study", Carbohydrate Research, Dec. 8, 2008, pp. 3021-3024, vol. 343, Issue 18, USA.
Asgari et al, "Dehydration of fructose to 5-hydroxymethylfurfural in sub-critical water over heterogeneous zirconium phosphate catalysts", Carbohydrate Research, vol. 341, Issue 14, Oct. 16, 2006, pp. 2379-2387.
Bao et al, "Preparation o f5-hydromethylfurfural by dehydration of fructose in the presense of acidic ionic liquid", Catalysis Communications, 2008, pp. 1383-1388.
Bicker et al, "Dehydration of d-fructose to hydroxymethylfurfural in sub- and supercritical fluids", The Journal of Supercritical Fluids, vol. 36, Issue 2, Dec. 2005, pp. 118-126.
Chheda et al, "Production of 5-hydroxymethylfurfural and furfural by dehydration of biomass-derived mono- and poly-saccharides", Green Chem., 2007,9, 342-350.
Halliday et al, "One-pot, two-step, practical catalytic syntehses of 2,5-diformylfuran from fructose", May 29, 2003, Organic Letters, USA.
Hamada et al, "An Improved Method for the Conversion of Saccharides Into Furfural Derivatives", Chemistry Letters, 1982, pp. 617-618, The Chemical Society of Japan.
Qi et al, "Catalytical conversion of fructose and glucose into 5-hydroxymethylfurfural in hot compressed water by microwave heating", Catalysis Communications, vol. 9, Issue 13, Jul. 20, 2008, pp. 2244-2249.
Srokol et al, "Hydrothermal upgrading of biomass to biofuel; studies on some monosaccharide model compounds", Carboydr Res., Jul. 12, 2004, vol. 39, Issue 10, pp. 1717-1726.
Szmant et al, "The preparation of 5-hydroxymethylfurfuraldehyde from high fructose corn syrup and other carbohydrates", Journal of Chemical Technology and Biotechnology, vol. 31, Issue 1, pp. 135-145, 1981.
Tyrlik et al, "Selective dehydration of glucose to hydroxymethylfurfural and a one-pot synthesis of a 4-acetylbutyrolactone from glucose and trioxane in solutions of aluminium salts", Carbohydrate Research, vol. 315, Issues 3-4, Feb. 28, 1999, pp. 268-272.
Villard et al, "Racemic and enantiopure synthesis and physicochemical characterization of the novel taste enhancer N-(1-carboxyethyl)-6-(hydroxymethyl)pyridinium-3-ol inner salt", J Agric Food Chem. Jul. 2, 2003;51(14):4040-5.
Yong et al, "Efficient Catalytic System for the Selective Production of 5-Hydroxymethylfurfural from Glucose and Fructose", Angewandte Chemie International Edition, vol. 47, Issue 48, pp. 9345-9348, Nov. 17, 2008.

* cited by examiner

*Primary Examiner* — Kristin Vajda
(74) *Attorney, Agent, or Firm* — Workman Nydegger

(57) ABSTRACT

A process for the production of furan derivatives from carbohydrates in the presence of an acidic catalyst, characterized in that N-methylpyrrolidone is used as a solvent and that the acidic catalyst is homogeneous.

19 Claims, 4 Drawing Sheets

PROCESS FOR THE PRODUCTION OF FURAN DERIVATIVES

The present invention relates to the production of furan derivatives from carbohydrates in the presence of an acidic catalyst.

Numerous processes for the production of furan derivatives from carbohydrates are known.

In such processes several different acidic catalysts are in use: classical inorganic acids, see e.g. Chheda, J. N.; Roman-Leshkow, Y.; Dumesic, J. A. Green Chem. 2007, 9, 342-350: organic acids (e.g. oxalic acid), H-form zeolites, transition metal ions, see e.g. Young, G.; Zhang, Y.; Ying, J. Y. Angew. Chem. Int. Ed. 2008, 47, 9345-9348; Tyrlik, S. K.; Szerszen, D.; Olejnik, M.; Danikiewicz, W. Carbohydr. Res. 1999, 315, 268-272; solid metal phosphates, see e.g. Asghari, F. S.; Yoshida, H. Carbohydr. Res. 2006, 341, 2379-2387; strong acid cation exchange resins, see e.g. Villard, R.; Robert, F.; Blank, I.; Bernardinelli, G.; Soldo, T.; Hofmann, T. J. Agric. Food Chem. 2003, 51, 4040-4045.

In such processes water as a solvent was intensively investigated as a green solvent. While the system containing biomass and water represents a green approach, on the other hand temperatures of >300° C. and pressures at around 20 MPa are required to achieve acceptable yields, see e.g. Qi, X.; Watanabe, M.; Aida, T. M.; Smith Jr., R. S. Cat. Commun. 2008, 9, 2244-2249.

A furan derivative which may be produced from carbohydrates in the presence of an acidic catalyst includes 5-hydroxymethylfurfural (HMF). Processes for the production of HMF are known. In aqueous solution, homogeneous and heterogenous acid catalysts can be used to produce HMF starting from carbohydrates. The achieved yields of HMF are between 30 to 60% depending on the carbohydrate source and the exact reaction conditions. Drawbacks when using water as a reaction solvent are the formation of byproducts, especially levulinic acid and insoluble humins. Furthermore these reactions must be carried out at very harsh conditions up to 300° C. and 27 MPa, see e.g. Bicker, M., Kaiser, D., Ott, L., Vogel, H., J. of Supercrit. Fluids 2005, 36, 118-126; Szmant, H. H., Chundury, D. D., J. Chem. Techn. Biotechnol. 1981, 31, 135-145; Srokol, Z., Bouche, A.-G., van Estrik, A., Strik, R. C. J., Maschmeyer, T., Peters, J. A., Carbohydr. Res. 2004, 339, 1717-1726). A flow process under supercritical conditions starting from glucose was described by Aida, T. A.; Sato, Y.; Watanabe, M.; Tajima, K.; Nonaka, T.; Hattori, H.; Arai, K. J. of Supercrit. Fluids, 2007, 40, 381-388.

Organic solvents may be suitable solvents also in the preparation of HMF, but a critical limitation is that such solvents may be difficult to separate from the product HMF, see e.g. Bao, Q.; Qiao, K.; Tomido, D.; Yokoyama, C. Catal. Commun. 2008, 9, 1383-1388; Halliday, G. A.; Young Jr., R. J.; Grushin, V. V. Org. Lett. 2003, 5, 2003-2005. Furthermore, previously employed organic solvents for HMF are not inert to subsequent reaction conditions to form HMF derivatives when the solvent is not separated from the HMF intermediate. Commonly employed organic solvents for the formation of HMF from carbohydrates are DMSO and dimethylformamide (DMF). In comparison to water as a solvent the reaction of carbohydrates to furan derivates can be carried out at lower temperatures (80-140° C.) and even with higher yields of HMF (up to 95% in DMSO) in short reaction times (30 min-2 h), see e.g. Halliday, G. A., Young Jr., R. J., Grushin, V. V., Org. Lett. 2003, 5, 2003-2005; WO 2009/076627 A2. Nevertheless, these polar organic solvents promote the dehydratization of fructose (and other carbohydrates) to HMF (and derivatives), as e.g. DMSO is also acting as a catalyst, see Amarasekara, A. S.; Williams, L. D.; Ebede, C. C. Carbohydr. Res. 2008, 343, 3021-3024.

Reaction mixtures of water/DMSO or water/toluene are known and also applied to continuous extraction, see e.g. Chheda, J. N., Roman-Leshkov, Y., Dumesic, J. A., Green Chem. 2007, 9, 342-350. The reaction takes between 4 to 6 hours at 140-180° C., resulting in 80% HMF yield at best.

Ionic liquids can act as neutral solvents but also as Brønsted acids and they can even be immobilized on silica gel, e.g. as disclosed in Bao, Q.; Qiao, K.; Tomido, D.; Yokoyama, C. Catal. Commun. 2008, 9, 1383-1388, but the separation of HMF and the ionic liquid still remains difficult.

All the known processes have drawbacks, e.g. harsh conditions if water is used as a solvent, or isolation issues if highly polar solvents such as DMF or DMSO are used which may result in high energy consumpting processes and/or which may result in insufficient purity/yield.

It was now found surprisingly that reaction conditions can be tempered which in consequence may increase the process efficiency, e.g. in terms of energy consumption, product purity, yields, suppression of humeric polymer production, if a specific organic solvent is used in the production of furan derivatives from carbohydrates under acidic, homogeneous catalysis.

In one aspect, the present invention provides a process for the production of furan derivatives from carbohydrates in the presence of an acidic catalyst, which is characterized in that N-methylpyrrolidone is used as a solvent and that the acidic catalyst is homogeneous.

A process provided by the present invention is herein also designated as "process of (according to) the present invention".

The use of N-methylpyrrolidone (NMP) as a solvent according to the present invention includes that NMP is used as the (sole) reaction solvent and that NMP is used as a reaction co-solvent, e.g. NMP may be used alone or in combination with other inorganic or organic solvent.

In another aspect the present invention provides a process according to the present invention, which is characterized in that N-methylpyrrolidone is used as the sole solvent; and in another aspect that N-methylpyrrolidone is used as a co-solvent.

A process of the present invention may be carried out as a batch process or as a continuous process, optionally under microwave irradiation.

In another aspect the present invention provides a process of the present invention which is characterized in that the process is carried out as a batch process or as a continuous process, optionally under microwave irradiation.

In a process of the present invention, a carbohydrate preferably is a sugar, e.g. a sugar which may be obtained from biomass, more preferably a sugar which may be dehydrated to obtain a furan derivative. Such sugars e.g. include C5 and C6 sugars, preferably C6 sugars, such as fructose, and natural and synthetic sugars, e.g. natural sugars, such as D-(−)-fructose.

In another aspect the present invention provides a process according to the present invention wherein the carbohydrate is a sugar, such as fructose, e.g. D-(−)-fructose.

In a process of the present invention, a furan derivative is preferably a furan substituted by an aldehyde, e.g. and further substituted by a hydroxy group, such as 5-hydroxymethylfurfural (HMF), e.g. of formula

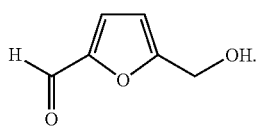

In another aspect, the present invention provides a process for the production of 5-hydroxymethylfurfural from a sugar, e.g. comprising dehydratization of a sugar, in the presence of a homogeneous acidic catalyst, wherein N-methylpyrrolidone is used as a solvent, e.g. or co-solvent.

In a process of the present invention an acidic homogenous catalyst is used. Useful acidic homogenous catalysts are listed in the preamble of the present application. In one preferred embodiment of the present invention a homogenous catalyst is an acid, e.g. an inorganic acid, such as HCl, $H_2SO_4$.

In another aspect the present invention provides a process of the present invention which is characterized in that an acid, e.g. an inorganic acid, such as HCl, $H_2SO_4$ is used as homogenous catalyst.

In a process of the present invention, the reaction temperature may be far below 300° C., e.g. in a range of 100 to 220° C., preferably from 125 to 200° C., more preferably from 140° C. to 170° C.

The reaction time of a reaction according to the present invention is dependent from the process used. In general the reaction time, however, is surprisingly short, e.g. from 30 seconds to 20 minutes, preferably from 1 minute to 10 minutes, more preferably from 2 to 6 minutes.

SHORT DESCRIPTION OF THE FIGURES (FIG. 1 TO FIG. 8)

In the following examples all temperatures are in degrees Celsius (° C.).

The following abbreviations are used (herein and in the examples):

| aqu. | aqueous | CMF | 5-Chloromethylfurfural |
|---|---|---|---|
| cons. | consumption | EtOAc | Ethyl acetate |
| HMF | 5-Hydroxymethylfurfural | HPLC | High performance liquid chromatography |
| h | hour(s) | | |
| IC | Interconversion | LA | Levulinic acid |
| min | minute(s) | NMP | N-Methylpyrrolidone |
| PDA | Photo Diode Array (Detector) | RI | Refractive Index (Detector) |
| rt | room temperature | | |
| Temp | Temperature | TFA | Trifluoroacetic acid |

2. Overview

Figure 7:
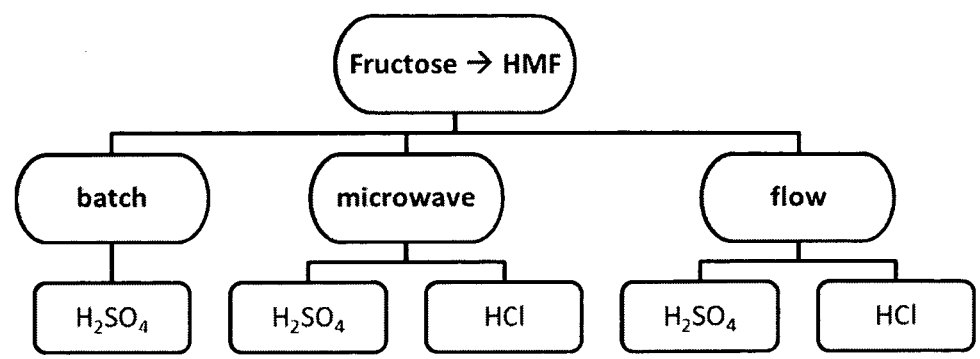
FIG. 7 shows a reaction scheme I (Fructose→IMF)

Dehydration reactions from fructose to HMF were carried out examining a variety of reaction conditions, using standard batch chemistry, but also microwave-assisted heating methods and continuous flow chemistry, as depicted in the Reaction Scheme I below. Surprisingly, NMP was found to be a most efficient solvent for this conversion compared to reported systems, in particular suitable for processes operating under homogeneous catalysis and under both, microwave and flow chemistry conditions. A reaction scheme is shown in FIG. 7.

3. Materials and Methods

All reactions and samples were prepared as double experiments.

3.1 Materials

D-(−)-Fructose, and 3-hydroxybenzyl alcohol were purchased from Fluka. Levulinic acid was used from Aldrich for calibration of by-product formation. Hydrochloric acid, as well as sulphuric acid were bought from Busetti and diluted to the desired concentrations. Anhydrous NMP was supplied by Merck.

3.2 Synthesis of HMF as Reference Material

For reference purposes, HMF was prepared in small analytical samples. Fructose was reacted to CMF according to Hamad, K., Yoshihara, H., Suzukamo, G., Chem. Lett. 1982, 617-618 and further converted to HMF via nucleophilic substitution:

CMF (2 g, 13.8 mmol) and deionized water (20 mL) were filled into a microwave vial and heated to 80° C. for 3 min. The solution obtained was extracted three times with EtOAc, the combined organic layers were washed with aqu. saturated $NaHCO_3$ solution and dried over anhydrous $Na_2SO_4$. After filtration of the solid, the solvent obtained was evaporated under reduced pressure to give crude product, which was further purified via chromatography ($SiO_2$, $CH_2Cl_2$:$CH_3OH$=95:5). Pure HMF in the form of a light yellow oil (1.12 g, 8.85 mmol, 64% of theory) was obtained which solidified upon storage at −30° C.

3.3 Batch Reactions

If not stated otherwise, all batch reactions were carried out in 4 mL glass vials with screw caps and heated in appropriate aluminium heating blocks maintaining the desired temperatures.

3.4 Microwave Batch Reactions

Microwave reactions in batch were performed using a Biotage Initiator Sixty laboratory microwave, equipped with an autosampler allowing sequential reactions. Absorption level was set to the highest possible setting and maximum irradiation power was automatically regulated to 400 W.

3.5 Stopped Flow Microwave and Continuous Flow Reactions

Stopped flow reactions to optimize for a semi-continuous microwave process were carried out in a CEM® Discover system with the CEM® Voyager upgrade and an external pressure sensor for reactions in small vials.

Reactions in continuous flow were performed in the cartridge-based reactor system X-Cube from ThalesNano®, supplied with a Gilson® GX-271 autosampler to allow for automated product collection. Two quartz sand cartridges (CatCart®, 70×4 mm) were installed as a reaction bed.

Figure 8:
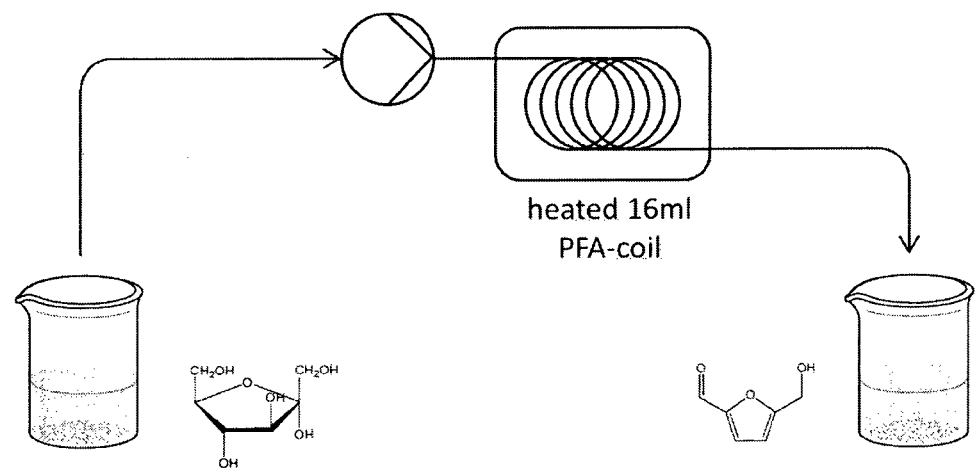
FIG. 8 shows a Reaction Scheme II with the exact setup.

Alternatively, a PFA (perfluoroalkoxy alkane) capillary (0.8 mm inner diameter, 1.6 mm outer diameter) was wrapped around an aluminium cylinder which was heated to the desired temperature. Starting materials were pumped using a Shimadzu LC-10AD HPLC pump at the appropriate flow rate. Exact volumes (column: 16.0 mL, pre- and post-volume: 1.0 mL each) were evaluated using a defined flow rate, a digital stop watch and pure solvent only. The exact setup is shown in FIG. 8.

3.5 Analysis

Reaction analysis was performed by HPLC on a Thermo Scientific® Surveyor Plus System equipped with a PDA Plus and RI detector or a Shimadzu® Nexera system equipped with the same detectors. For the separation, an ion-exclusion column from Phenomenex® (Rezex RHM-Monosaccharide H+ (8%), 150×7.8 mm, sulfonated styrene divinyl benzene matrix, hydrogen ionic form) was used running on HPLC-grade water/0.1% HPLC-grade TFA as a mobile phase. The run temperature was adjusted to 85° C. and run time was optimized to 25 minutes. Product quantification was achieved by an internal standard method and RI detection, discrete PDA wavelengths were set to 200 nm, 254 nm and 280 nm for further evaluation of the reactions.

4. General Procedures 4.1. Preparation of HPLC Samples

To allow for accurate HPLC quantification, all reaction samples were diluted to a maximum carbohydrate concentration of 2 mg/mL. A sample (22 µL) was dissolved in deionized water (978 µL), internal standard (100 µL 3-hydroxybenzyl alcohol) was added and the sample was mixed thoroughly. Solid residues were separated by centrifugation (5 min, 20.000 g) or filtration (Phenex PTFE, 4 mm, 0.2 µm) and quantification of carbohydrates and products was achieved via refractive index detection on HPLC.

For reaction samples having a different concentration, the dilution values were adapted appropriately to ensure not to exceed a maximum concentration of 2 mg/mL.

4.2 GP1—Fructose Dehydratization in Batch

As a standard procedure, fructose (100 mg, 555 µmol) and catalyst were loaded into a glass vial, equipped with a magnetic stirring bar. Freshly distilled NMP (1 mL) was added and the reaction solution obtained was stirred at the selected temperature.

4.3 GP2—Fructose Dehydratization in the Microwave

Fructose (100 mg, 555 µmol) and catalyst were loaded into a microwave vial (0.5-2.0 mL size) and equipped with a magnetic stirring bar. NMP (1 mL) was added and irradiation power was automatically adjusted by the microwave's regulation algorithms. An appropriate cooling rate was achieved by supplying pressurized air with a pressure of at least 6 bar to directly cool the microwave vessel.

4.4 GP3—Fructose Dehydratization in Stopped Flow Microwave Reactor Systems

Fructose stock solution (1 mL; c=100 mg/mL in NMP) and hydrochloric acid (100 µL; c=1 mol/L) were charged into a microwave vial equipped with a magnetic stirring bar. After sealing the vial with a snap-cap, the reaction solution was heated adjusting the desired reaction temperature and duration. To ensure for a rapid heating process, coupling power was adjusted according to the following Table 1:

TABLE 1

| Temperature (° C.) | Power Rating (W) |
|---|---|
| 100 | 50 |
| 125 | 65 |
| 150 | 100 |
| 180 | 125 |
| 200 | 140 |
| 220 | 160 |

An appropriate cooling rate was achieved by supplying pressurized air with a pressure of at least 6 bar to directly cool the microwave vessel.

4.5 GP4—Fructose Dehydratization in Cartridge-Based Reactor Systems

Fructose stock solution (c=100 mg/mL in NMP) was mixed with hydrochloric acid (c=1 mol/L) and supplied to the reactor system via reagent pump A. During the heating process, several pre-samples were collected to guarantee for a stable temperature and flow rate. Reaction temperatures were selected at 150° C., 180° C. and 200° C., pressure during the reactions was regulated to 40 bar, flow rates were adjusted from 0.2 mL/min to 0.6 mL/min and collected fractions to 2.5 mL each.

5. Results & Discussion 5.1 Experiments Performed in Batch Using Sulphuric Acid as a Catalyst To evaluate the dehydration properties of sulphuric acid in NMP, a variety of temperatures and acid concentrations was examined. Samples were prepared according to GP1 using either 100 µL 1N sulphuric acid solution or 10 µL concentrated sulphuric acid as catalyst, leading to the following results set out in Table 2 below:

TABLE 2

| Catalyst | Temp. | Reaction time | Fructose cons. | HMF yield | HMF selectivity | LA yield |
|---|---|---|---|---|---|---|
| 1N $H_2SO_4$ | 100° C. | 3 h | 69% | 45% | 65% | <1% |
| 1N $H_2SO_4$ | 120° C. | 4 h | 95% | 77% | 81% | <1% |
| 1N $H_2SO_4$ | 150° C. | 15 min | 98% | 88% | 90% | <1% |
| 1N $H_2SO_4$ | 180° C. | 10 min | 100% | 85% | 85% | <1% |
| $H_2SO_4$ conc. | 120° C. | 45 min | 98% | 85% | 90% | <1% |
| $H_2SO_4$ conc. | 150° C. | 10 min | 100% | 90% | 90% | <1% |
| $H_2SO_4$ conc. | 180° C. | 5 min | 100% | 82% | 82% | <1% |

Figure 1:
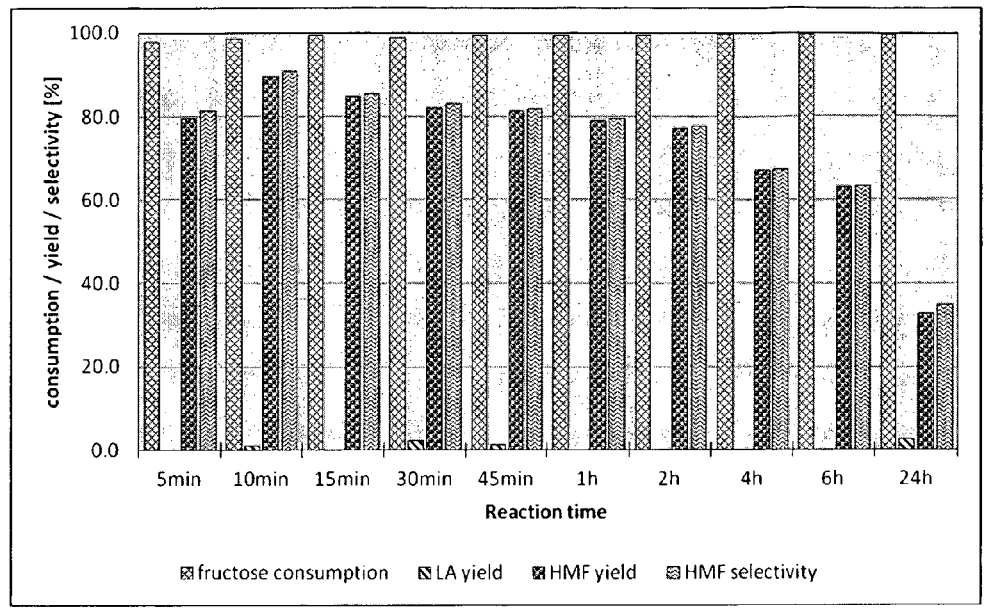
FIG. 1 shows the results of a time screening in an experiment performed in batch with sulphuric acid as a catalyst according to 5.1.

Formation of black, insoluble polymers and humins were not observed under the applied, optimal conditions. To characterize the exact progress of the dehydratization, time screenings were performed. A representative time course is shown in FIG. 1 ($H_2SO_4$ conc., 150° C.).

5.2 Experiments Performed in the Microwave 5.2.1 Sulphuric Acid as a Catalyst

Figure 2:
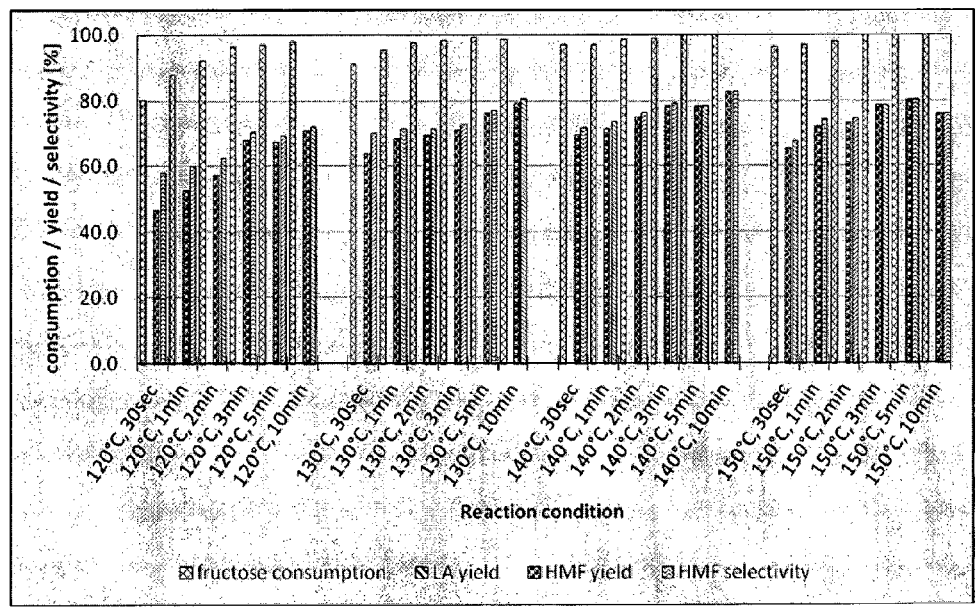
FIG. 2 and FIG. 3 show results of experiments performed in the microwave with sulphuric acid as catalyst according to 5.2.1.
Figure 3:
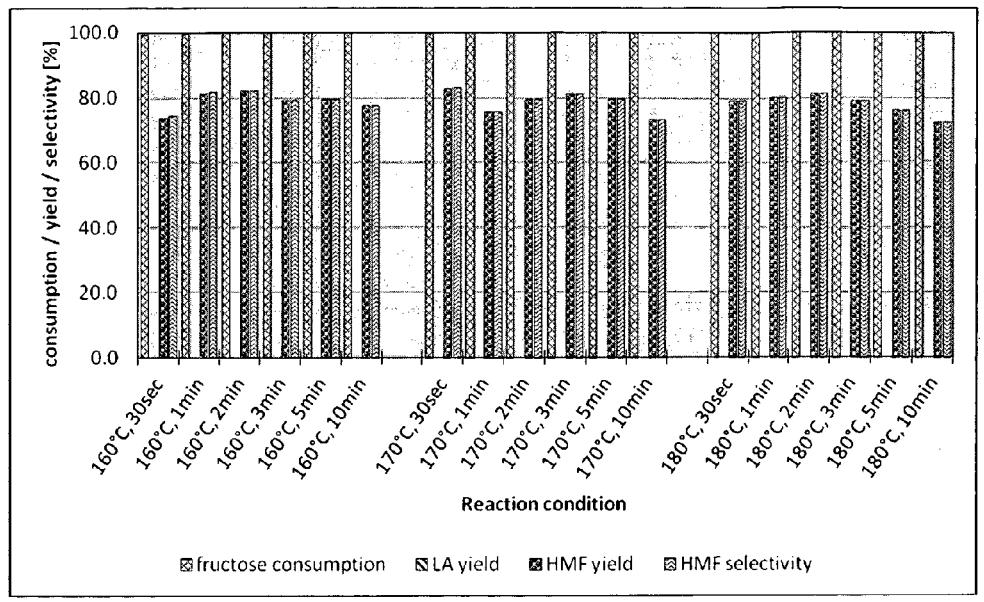

To precisely control heating, steady-state and cooling phases during the dehydratization reactions, also microwave-assisted heating was applied. The samples were prepared as mentioned in GP2 using NMP as a solvent. No formation of black tar was observed under the defined reaction conditions. Furthermore, a trend towards lower reaction time and higher temperature was clearly visible, leading to full fructose conversion and a maximum HMF yield of 83%. Results are set out in FIG. 2 and FIG. 3.

5.2.2 Hydrochloric Acid as a Catalyst

Figure 4:
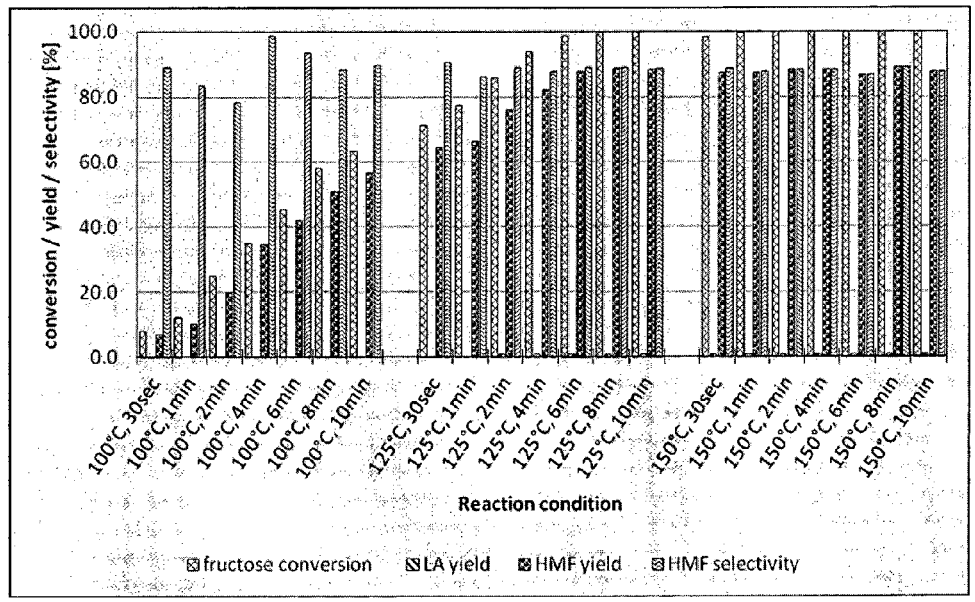
FIG. 4 and FIG. 5 show results of experiments performed in the microwave with hydrochloric acid as catalyst according to 5.2.2.
Figure 5:
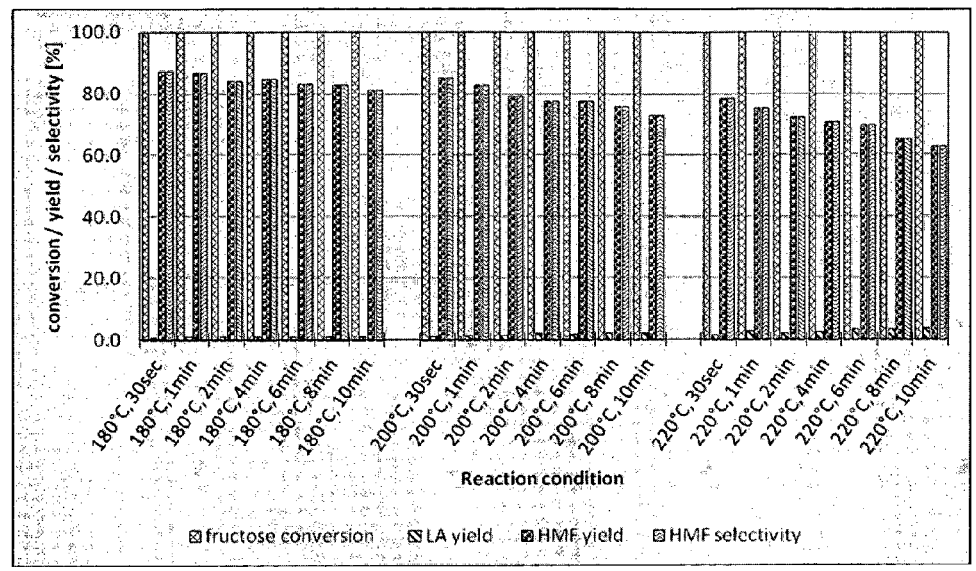

Fructose dehydratization in a stopped flow microwave using NMP was performed according to GP3. The progress of starting material consumption and product/by-product formation follows a strict trend, leading to full fructose conversion and a maximum HMF yield of 89%. Results see in FIG. 4 and FIG. 5.

5.3 Experiments Performed in Flow (Continuous Process)

5.3.1 Sulphuric Acid as a Catalyst

Fructose (10% m/v) and concentrated sulphuric acid (1% v/v) were dissolved in NMP and supplied to the PFA capillary continuous flow reactor setup. Samples were prepared by passing 18 mL of solution through the reactor to the waste and collecting subsequent 10 mL of product solution into glass vials, both at 150° C. as target temperature. Results are set out in Table 3 below:

TABLE 3

| Flow rate (mL/min) | Residence time (min) | Fructose cons. | HMF yield | HMF selectivity | LA yield |
|---|---|---|---|---|---|
| 0.8 | 20 | 100% | 74% | 74% | <1% |
| 1.6 | 10 | 100% | 75% | 75% | <1% |
| 3.2 | 5 | 100% | 76% | 76% | <1% |

Formation of black, insoluble polymers and humins were not observed under the applied conditions.

5.3.2 Hydrochloric Acid as a Catalyst

Figure 6:
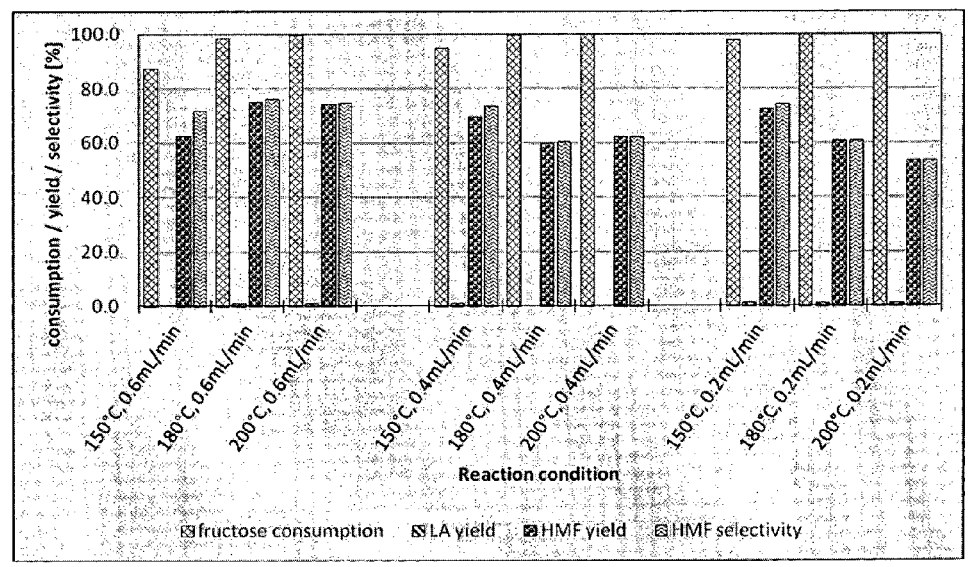
FIG. 6 shows results shows results of experiments performed in flow (continuous process) with hydrochloric acid as a catalyst according to 5.3.2.

Finally, dehydratization properties of hydrochloric acid in NMP under continuous flow conditions were evaluated according to GP4. Maximum HMF yield of 75% could be achieved at 180° C. and 0.6 mL/min, giving a product selectivity of 76%. Levulinic acid yield was mostly below 1%. Results are set out in FIG. 6.

6. Comparative Example

Heterogeneous AlCl$_3$ as a Catalyst

To test also a Lewis acid catalyst in the same setup (GP1), freshly sublimed aluminium trichloride and NMP were chosen as representative candidates. The catalyst is prone to hydrolysis and therefore lacks applicability in a repeated or continuous conversion. Additionally massive formation of black tar was monitored. See e.g., Table 4 below:

TABLE 4

| Catalyst amount | Temp. (° C.) | Reaction time | Fructose cons. | HMF yield | HMF selectivity | LA yield |
|---|---|---|---|---|---|---|
| 10 mg | 1000 | 3 h | 100% | 50% | 50% | <1% |

From that example it is evident that a heterogenous catalyst as AlCl$_3$ has by far much less conversion activity than a homogenous catalyst in a process according to the present invention. Moreover, purity of the product obtained is rather decreased compared with the purity of a product obtained with a homogenous catalyst according to the present invention.

The invention claimed is:

1. A process for the production of furan derivatives from one or more carbohydrates in the presence of an acidic catalyst, wherein N-methylpyrrolidone is used as a co-solvent and the acidic catalyst is homogeneous, and wherein the process is carried out as a continuous process at a temperature from about 100° C. to about 220° C., with a reaction time from about 30 seconds to about 20 minutes.

2. The process according to claim 1, wherein the furan derivative is 5-hydroxymethylfurfural.

3. The process according to claim 1, wherein the one or more carbohydrates comprise at least one sugar.

4. The process according to claim 3, wherein the one or more carbohydrates comprise fructose.

5. The process according to claim 1, wherein the acid catalyst is an acid.

6. The process according to claim 5, wherein the acid is sulphuric acid or hydrochloric acid.

7. The process according to claim 1, wherein the reaction is carried out at a temperature from 125 to 200° C.

8. The process according to claim 7, wherein the reaction is carried out at a temperature from 140° C. to 170° C.

9. The process according to claim 1, wherein the reaction time is from 1 minute to 10 minutes.

10. The process according to claim 9, wherein the reaction time is from 2 to 6 minutes.

11. A process for the production of furan derivatives from one or more carbohydrates in the presence of an acidic catalyst, wherein N-methylpyrrolidone is used as a solvent and the acidic catalyst is homogeneous, and wherein the process is carried out as a continuous process at a temperature from about 100° C. to about 220° C., with a reaction time from 1 minute to 10 minutes.

12. The process according to claim 11, wherein the furan derivative is 5-hydroxymethylfurfural.

13. The process according to claim 11, wherein the one or more carbohydrates comprise at least one sugar.

14. The process according to claim 13, wherein the one or more carbohydrates comprise fructose.

15. The process according to claim 11, wherein the acid catalyst is an acid.

16. The process according to claim 15, wherein the acid is sulphuric acid or hydrochloric acid.

17. The process according to claim 11, wherein the reaction is carried out at a temperature from 125 to 200° C.

18. The process according to claim 17, wherein the reaction is carried out at a temperature from 140° C. to 170° C.

19. The process according to claim 11, wherein the reaction time is from 2 to 6 minutes.

* * * * *

UNITED STATES PATENT AND TRADEMARK OFFICE
CERTIFICATE OF CORRECTION

PATENT NO. : 9,475,787 B2  
APPLICATION NO. : 14/424372  
DATED : October 25, 2016  
INVENTOR(S) : Mihovilovic et al.

Page 1 of 1

It is certified that error appears in the above-identified patent and that said Letters Patent is hereby corrected as shown below:

In the Specification

Column 2
Line 18, change "energy consumpting processes" to --energy consuming processes--

Column 3
Line 44, change "shows results shows results of experiments" to --shows results of experiments--

Column 7
Line 41, change "catalyst as" to --catalyst such as--

Signed and Sealed this
Ninth Day of May, 2017

Michelle K. Lee
*Director of the United States Patent and Trademark Office*